US012751968B2

(12) United States Patent
Shah et al.

(10) Patent No.: US 12,751,968 B2
(45) Date of Patent: Oct. 6, 2026

(54) PULMONARY ARTERIAL COMPLIANCE WITH INHALED NITRIC OXIDE (iNO) TREATMENT

(71) Applicant: Mallinckrodt Pharmaceuticals Ireland Limited, Dublin (IE)

(72) Inventors: Parag Shah, Morristown, NJ (US); Peter Fernandes, Randolph, NJ (US)

(73) Assignee: Mallinckrodt Pharmaceuticals Ireland Limited, Dublin (IE)

(*) Notice: Subject to any disclaimer, the term of this patent is extended or adjusted under 35 U.S.C. 154(b) by 886 days.

(21) Appl. No.: 17/796,451

(22) PCT Filed: Jan. 27, 2021

(86) PCT No.: PCT/US2021/015257
§ 371 (c)(1),
(2) Date: Jul. 29, 2022

(87) PCT Pub. No.: WO2021/154833
PCT Pub. Date: Aug. 5, 2021

(65) Prior Publication Data

US 2023/0067942 A1 Mar. 2, 2023

Related U.S. Application Data

(60) Provisional application No. 62/968,424, filed on Jan. 31, 2020.

(51) Int. Cl.
*A61K 33/00* (2006.01)
*A61P 9/00* (2006.01)
*A61P 11/00* (2006.01)

(52) U.S. Cl.
CPC ................ *A61K 33/00* (2013.01); *A61P 9/00* (2018.01); *A61P 11/00* (2018.01)

(58) Field of Classification Search
None
See application file for complete search history.

(56) References Cited

U.S. PATENT DOCUMENTS

2012/0093948 A1* 4/2012 Fine ........................ A61P 25/34 424/718

FOREIGN PATENT DOCUMENTS

| | | | |
|---|---|---|---|
| JP | H1036273 | A | 2/1998 |
| WO | 2013138654 | A1 | 9/2013 |
| WO | 2016000653 | A1 | 1/2016 |
| WO | 2019133777 | A1 | 7/2019 |
| WO | 2019222640 | A1 | 11/2019 |

OTHER PUBLICATIONS

Barst R. J., et al., "Clinical Perspectives with Long-Term Pulsed Inhaled Nitric Oxide for the Treatment of Pulmonary Arterial Hypertension," Pulmonary Circulation, Apr. 2012, vol. 2, No. 2, pp. 139-147, DOI: 10.4103/2045-8932.97589.

First Office Action and Search Report for Chinese Patent Application No. 202180010455.X, dated Oct. 12, 2024, 20 pages.

Office Action for Japanese Patent Application No. 2022-544737, mailed on Dec. 25, 2024, 4 pages.

Su J., et al., "Nitric Oxide Attenuates Arterial Pulse Wave Reflection in a Vasodilator Responding Pulmonary Arterial Hypertension Patient," Circulation: Cardiovascular Interventions, Mar. 2018, vol. 11, No. 3, 3 pages, DOI: 10.1161/CIRCINTERVENTIONS.117.006242.

Vonbank K., et al., "Controlled Prospective Randomised Trial on the Effects on Pulmonary Haemodynamics of the Ambulatory Long Term Use of Nitric Oxide and Oxygen in Patients with Severe COPD," Thorax, Apr. 1, 2003, vol. 58, No. 4, pp. 289-293.

Warren N. J., Bellerophon Announces Positive Initial Data from Acute Hemodynamic Dose Escalation Study of INOpulse for Treatment of Pulmonary Hypertension Associated with Interstitial Lung Disease, Bellerophon Therapeutics, Nov. 12, 2019, 2 pages, Retrieved from the Internet URL: https://www.biospace.com/bellerophon-announces-positive-initial-data-from-acute-hemodynamic-dose-escalation-study-of-inopulse-for-treatment-of-pulmonary-hypertension-associated-with-interstitial-lung-disease.

Williamson D. J., et al., "Acute Hemodynamic Responses to Inhaled Nitric Oxide in Patients With Limited Scleroderma and Isolated Pulmonary Hypertension," Circulation, Aug. 1, 1996, vol. 94, No. 3, pp. 477-482, DOI: 10.1161/01.cir.94.3.477.

International Search Report mailed Apr. 2, 2021 for International Patent Application No. PCT/US2021/015257, 3 pages.

Written Opinion mailed mailed Apr. 2, 2021 for International Patent Application No. PCT/US2021/015257, 4 pages.

Roberts Jr et al., Inhaled Nitric Oxide in Congenital Heart Disease, Circulation, vol. 87, No. 2, Feb. 1993, pp. 447-453.

Simon et al., Acute hemodynamic effects of inhaled sodium nitrite in pulmonary hypertension associated with heart failure with preserved ejection fraction, Clinical Medicine, Nov. 3, 2016, pp. 1-13.

International Preliminary Report on Patentability issued Jul. 28, 2022, in connection with International Patent Application No. PCT/US2021/015257 (5 pages).

Office Action for Chinese Application No. 202180010455.X, dated Jun. 28, 2025, 12 pages.

Bellerophon Therapeutics, Inc., "Bellerophon Announces Positive Initial Data from Acute Hemodynamic Dose Escalation Study of INOpulse for Treatment of Pulmonary Hypertension Associated with Interstital Lung Disease," Nov. 12, 2019, 4 pages.

Kusuda S., et al., "Contribution of Pulmonary Surfactant with Inhaled Nitric Oxide for Treatment of Pulmonary Hypertension," Pediatrics International, Oct. 2006, vol. 48(5), pp. 459-463.

Office Action for Japanese Patent Application No. 2022-544737, mailed on Jul. 30, 2025, 5 pages (p. 3-4 English).

Bellerophon Therapeutics, Inc (Mar. 15, 2018). "Annual report pursuant to Section 13 or 15(d) of the Securities Exchange Act of 1934 (Form 10-K)". U.S. Securities and Exchange Commission, https://www.secgov/Archives/edgar/data/1600132/000160013218000034/blph-12312017x10k.htm.

Hajian, B, et al. "Pulmonary vascular effects of pulsed inhaled nitric oxide in COPD patients with pulmonary hypertension". Int J Chron Obstruct Pulmon Dis. (Jul. 5, 2016); 11:1533-41. DOI: 10.2147/COPD.S106480.

(Continued)

*Primary Examiner* — Robert A Wax
*Assistant Examiner* — Quanglong N Truong
(74) *Attorney, Agent, or Firm* — Polsinelli PC

(57) ABSTRACT

Described are methods for reducing pulmonary resistance, reducing pulmonary pressure, and increasing pulmonary arterial compliance by providing a inhaled nitric oxide.

17 Claims, 2 Drawing Sheets

(56) References Cited

OTHER PUBLICATIONS

Silva, Patricia, "INOpulse—Cardiopulmonary Product", Pulmonary Hypertension News, Dec 6, 2019, (accessed Aug. 5, 26) https://web.archive.org/web/20191206024619/https://pulmonaryhypertension-news.com/inopulse-cardiopulmonary-product/.

* cited by examiner

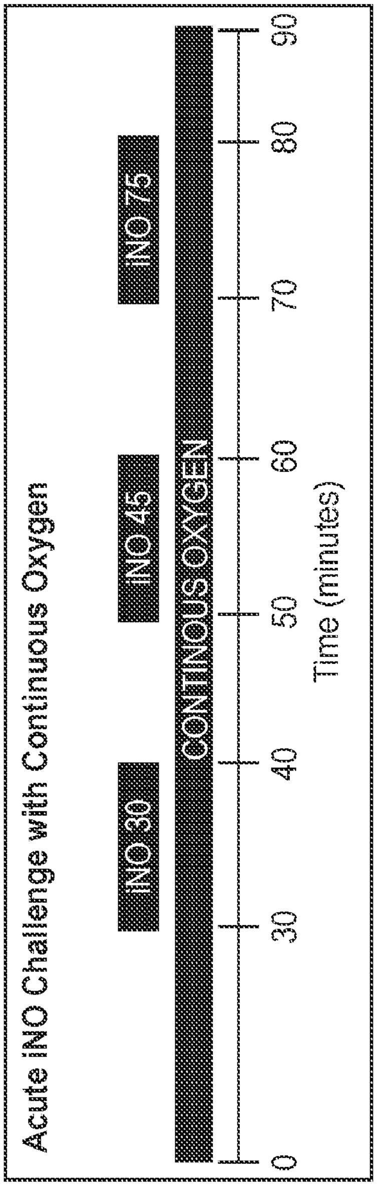
FIG. 1
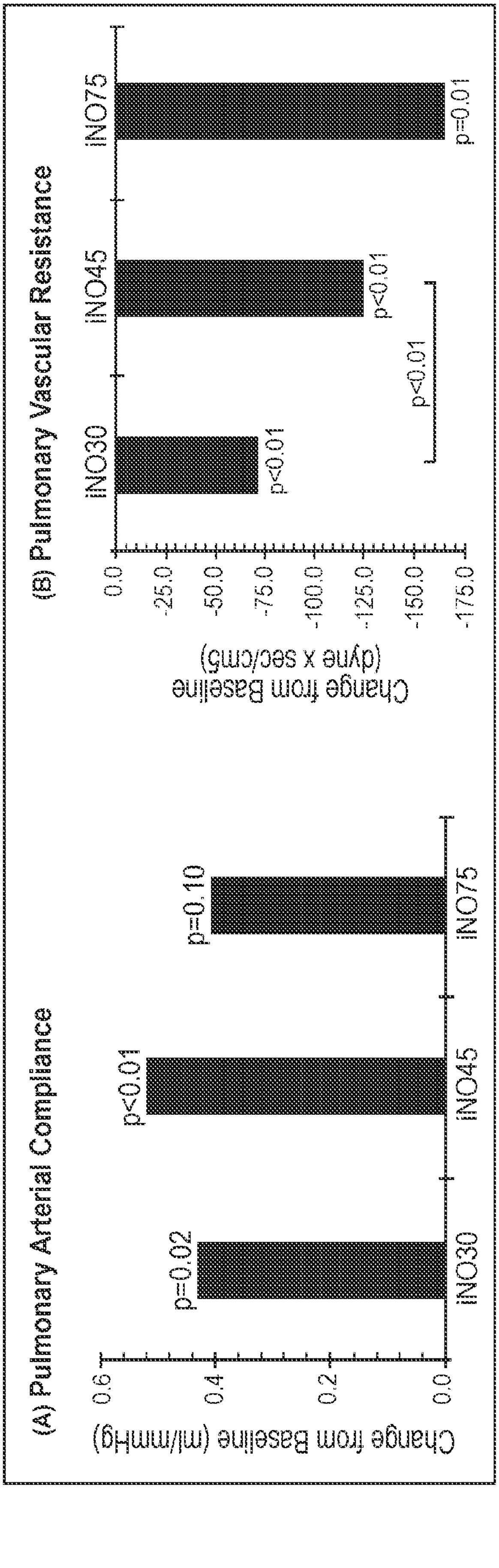
FIG. 2A
FIG. 2B

PULMONARY ARTERIAL COMPLIANCE WITH INHALED NITRIC OXIDE (iNO) TREATMENT

CROSS-REFERENCE TO RELATED APPLICATIONS

This application is a U.S. National Stage Entry of International Patent Application Serial No. PCT/US2021/015257, filed on Jan. 27, 2021, which in turn claims the benefit of U.S. Provisional Patent Application No. 62/968,424, filed Jan. 31, 2020, entitled "Improvement in Pulmonary Arterial Compliance with Inhaled Nitric Oxide (iNO) Treatment," each of which is incorporated by reference herein in its entirety.

FIELD OF THE INVENTION

The present application relates generally to use of inhaled nitric oxide (iNO) to improve pulmonary arterial compliance by decreasing pulmonary pressure (mPAP) and pulmonary resistance (PVR).

BACKGROUND OF THE INVENTION

Nitric oxide (NO) is a gas that, when inhaled, acts to dilate blood vessels in the lungs, improving oxygenation of the blood and reducing pulmonary hypertension. Because of this, nitric oxide is provided as a therapeutic gas in the inspiratory breathing phase for patients who experience shortness of breath (dyspnea) due to a disease state, for example, pulmonary arterial hypertension (PAH), chronic obstructive pulmonary disease (COPD), combined pulmonary fibrosis and emphysema (CPFE), cystic fibrosis (CF), idiopathic pulmonary fibrosis (IPF), emphysema, interstitial lung disease (ILD), chronic thromboembolic pulmonary hypertension (CTEPH), chronic high altitude sickness, or other lung disease.

While NO may be therapeutically effective when administered under the appropriate conditions, it can also become toxic if not administered correctly. NO reacts with oxygen to form nitrogen dioxide ($NO_2$), and $NO_2$ can be formed when oxygen or air is present in the NO delivery conduit. $NO_2$ is a toxic gas which may cause numerous side effects, and the Occupational Safety & Health Administration (OSHA) provides that the permissible exposure limit for general industry is only 5 ppm. Thus, it is desirable to limit exposure to $NO_2$ during NO therapy.

Effective dosing of NO is based on a number of different variables, including quantity of drug and the timing of delivery. Several patents have been granted relating to NO delivery, including U.S. Pat. Nos. 7,523,752; 8,757,148; 8,770,199; and 8,803,717, and a Design Patent D701,963 for a design of an NO delivery device, all of which are herein incorporated by reference. Additionally, there are pending applications relating to delivery of NO, including US2013/0239963 and US2016/0106949, both of which are herein incorporated by reference. Even in view of these patents and pending publications, there is still a need for methods and apparatuses that deliver NO in a precise, controlled manner, so as to maximize the benefit of a therapeutic dose and minimize the potentially harmful side effects.

SUMMARY OF THE INVENTION

In an embodiment of the invention, a method of reducing pulmonary pressure comprising delivering to a patient one or more doses of inhaled nitric oxide over a time period is described.

In another embodiment of the invention, a method of reducing pulmonary resistance comprising delivering to a patient one or more doses of inhaled nitric oxide over a time period is described.

In yet another embodiment, a method of increasing arterial compliance comprising delivering to a patient one or more doses of inhaled nitric oxide over a time period is described.

In another embodiment, the time period for delivering one or more doses of inhaled nitric oxide is 5, 10, 15, 20, 25, 30, 35, 40, 45, 50, 55, 60, 65, 70, 75, 80, 85, or 90 minutes. In another embodiment, the dose of inhaled nitric oxide is a dose-escalating pulsed dose. In another embodiment, the dose of inhaled nitric oxide is one or more of a iNO30, iNO45, iNO75, and iNO125.

BRIEF DESCRIPTION OF THE DRAWINGS

The foregoing summary, as well as the following detailed description of the invention, will be better understood when read in conjunction with the appended drawings.

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 1 depicts the study design for acute iNO dose escalation. Nine PH-PF subjects were administered escalating doses of pulsed iNO (iNO30 to iNO75 mcg/kg IBW/hrs) with continuous oxygen.

FIG. 2, comprising FIGS. 2A-2C, are graphs depicting pulmonary arterial compliance, or PAC (FIG. 2A), pulmonary vascular resistance, or PVR (FIG. 2B), and mean pulmonary arterial pressure, or mPAP (FIG. 2C) for inhaled nitric oxide at 30 mcg/kg IBW/hr (iNO30), 45 mcg/kg IBW/hr (iNO45), and 75 mcg/kg IBW/hr (iNO75). The data is based on nine pulmonary hypertension—interstitial lung disease (ILD) patients. Bar graphs represent median change from baseline at each assessment for all available subjects. FIG. 2A shows all doses demonstrate improvement in PAC, with the change in iNO30 and iNO45 being statistically significant. Likewise, FIG. 2B demonstrates statistically significant improvement in PVR in all iNO doses, with additional statistically significant improvement between iNO30 and iNO45 doses. FIG. 2C demonstrates statistically significant improvement in all doses of iNO for mPAP compared to baseline. Statistical analysis was based on the Wilcoxon Rank Test.

DETAILED DESCRIPTION OF THE INVENTION

Figure 2C:
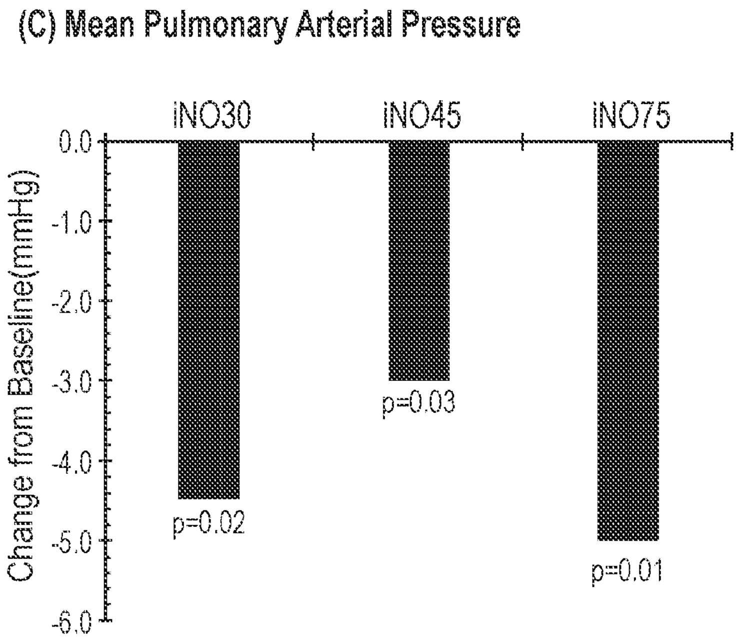

Unless defined otherwise, all technical and scientific terms used herein have the same meaning as is commonly understood by one of skill in the art to which this invention belongs. All patents and publications referred to herein are incorporated by reference in their entireties.

Before describing several exemplary embodiments of the invention, it is to be understood that the invention is not limited to the details of construction or process steps set forth in the following description. The invention is capable of other embodiments and of being practiced or being carried out in various ways.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

Definitions

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

The disease state of "interstitial lung disease" or "ILD" shall include all subtypes of ILD, including, but not limited to, idiopathic interstitial pneumonia (IIP), chronic hypersensitivity pneumonia, occupational or environmental lung disease, idiopathic pulmonary fibrosis (IPF), non-IPF IIPs, granulomoutus (e.g., sarcoidosis), connective tissue disease related ILD, and other forms of ILD.

When ranges are used herein to describe an aspect of the present invention, for example, dosing ranges, amounts of a component of a formulation, etc., all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, preferably from 0% to 10%, more preferably from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

For the avoidance of doubt, it is intended herein that particular features (for example integers, characteristics, values, uses, diseases, formulae, compounds or groups) described in conjunction with a particular aspect, embodiment or example of the invention are to be understood as applicable to any other aspect, embodiment or example described herein unless incompatible therewith. Thus such features may be used where appropriate in conjunction with any of the definition, claims or embodiments defined herein. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any disclosed embodiments. The invention extends to any novel one, or novel combination, of the features disclosed in this specification (including any accompanying claims, abstract and drawings), or to any novel one, or any novel combination, of the steps of any method or process so disclosed.

With respect to the present invention, in certain embodiments, a dose of a gas (e.g., NO) is administered in a pulse to a patient during an inspiration by the patient. It has been surprisingly discovered that nitric oxide delivery can be precisely and accurately delivered within the first two-thirds of total breath inspiration time and the patient obtains benefits from such delivery. Such delivery minimizes loss of drug product and risk of detrimental side effects increases the efficacy of a pulse dose which in turn results in a lower overall amount of NO that needs to be administered to the patient in order to be effective. Such delivery is useful for the treatment of various diseases, such as but not limited to idiopathic pulmonary fibrosis (IPF), pulmonary arterial hypertension (PAH), including Groups I-V pulmonary hypertension (PH), chronic obstructive pulmonary disease (COPD), combined pulmonary fibrosis and emphysema (CPFE), cystic fibrosis (CF), emphysema, interstitial lung disease (ILD), chronic thromboembolic pulmonary hypertension (CTEPH), chronic high altitude sickness, or other lung disease, and is also useful as an antimicrobial, for example, in treating pneumonia.

Such precision has further advantages in that only portions of the poorly ventilated lung area is exposed to NO. Hypoxia and issues with hemoglobin may also be reduced with such pulsed delivery, while $NO_2$ exposure is also more limited.

Breath Patterns, Detection and Triggers

Breath patterns vary based on the individual, time of day, level of activity, and other variables; thus it is difficult to predetermine a breath pattern of an individual. A delivery system that delivers therapeutics to a patient based on breath pattern, then, should be able to handle a range of potential breath patterns in order to be effective.

In certain embodiments, the patient or individual can be any age, however, in more certain embodiments the patient is sixteen years of age or older.

In an embodiment of the invention, the breath pattern includes a measurement of total inspiratory time, which as used herein is determined for a single breath. However, depending on context "total inspiratory time" can also refer to a summation of all inspiratory times for all detected breaths during a therapy. Total inspiratory time may be observed or calculated. In another embodiment, total inspiratory time is a validated time based on simulated breath patterns.

In an embodiment of the invention, breath detection includes at least one and in some embodiments at least two separate triggers functioning together, namely a breath level trigger and/or a breath slope trigger.

In an embodiment of the invention, a breath level trigger algorithm is used for breath detection. The breath level trigger detects a breath when a threshold level of pressure (e.g., a threshold negative pressure) is reached upon inspiration.

In an embodiment of the invention, a breath slope trigger detects breath when the slope of a pressure waveform indicates inspiration. The breath slope trigger is, in certain instances, more accurate than a threshold trigger, particularly when used for detecting short, shallow breaths.

In an embodiment of the invention, a combination of these two triggers provides overall a more accurate breath detection system, particularly when multiple therapeutic gases are being administered to a patient simultaneously.

In an embodiment of the invention, the breath sensitivity control for detection of either breath level and/or breath slope is fixed. In an embodiment of the invention, the breath sensitivity control for detection of either breath level or breath slope is adjustable or programmable. In an embodiment of the invention, the breath sensitivity control for either breath level and/or breath slope is adjustable from a range of least sensitive to most sensitive, whereby the most sensitive setting is more sensitive at detecting breaths than the least sensitive setting.

In certain embodiments where at least two triggers are used, the sensitivity of each trigger is set at different relative levels. In one embodiment where at least two triggers are used, one trigger is set a maximum sensivity and another trigger is set at less than maximum sensitivity. In one embodiment where at least two triggers are used and where one trigger is a breath level trigger, the breath level trigger is set at maximum sensivity.

Oftentimes, not every inhalation/inspiration of a patient is detected to then be classified as an inhalation/inspiration event for the administration of a pulse of gas (e.g., NO). Errors in detection can occur, particularly when multiple gases are being administered to a patient simultaneously, e.g., NO and oxygen combination therapies.

Embodiments of the present invention, and in particular an embodiment which incorporates a breath slope trigger alone or in combination with another trigger, can maximize the correct detection of inspiration events to thereby maximize the effectiveness and efficiency of a therepy while also minimizing waste due to misidentification or errors in timing.

In certain embodiments, greater than 50% of the total number of inspirations of a patient over a timeframe for gas delivery to the patient are detected. In certain embodiments, greater than 75% of the total number of inspirations of a patient are detected. In certain embodiments, greater than 90% of the total number of inspirations of a patient are detected. In certain embodiments, greater than 95% of the total number of inspirations of a patient are detected. In certain embodiments, greater than 98% of the total number of inspirations of a patient are detected. In certain embodiments, greater than 99% of the total number of inspirations of a patient are detected. In certain embodiments, 75% to 100% of the total number of inspirations of a patient are detected.

Dosages and Dosing Regimens

In an embodiment of the invention, nitric oxide delivered to a patient is formulated at concentrations of about 3 to about 18 mg NO per liter, about 6 to about 10 mg per liter, about 3 mg NO per liter, about 6 mg NO per liter, or about 18 mg NO per liter. The NO may be administered alone or in combination with an alternative gas therapy. In certain embodiments, oxygen (e.g., concentrated oxygen) can be administered to a patient in combination with NO.

In an embodiment of the present invention, a volume of nitric oxide is administered (e.g., in a single pulse) in an amount of from about 0.350 mL to about 7.5 mL per breath. In some embodiments, the volume of nitric oxide in each pulse dose may be identical during the course of a single session. In some embodiments, the volume of nitric oxide in some pulse doses may be different during a single timeframe for gas delivery to a patient. In some embodiments, the volume of nitric oxide in each pulse dose may be adjusted during the course of a single timeframe for gas delivery to a patient as breath patterns are monitored. In an embodiment of the invention, the quantity of nitric oxide (in ng) delivered to a patient for purposes of treating or alleviating symptoms of a pulmonary disease on a per pulse basis (the "pulse dose") is calculated as follows and rounded to the nearest nanogram value:

Dose mcg/kg-IBW/hr×Ideal body weight in kg (kg-IBW)×((1 hr/60 min)/(respiratory rate (bpm))×(1,000 ng/mcg).

As an example, Patient A at a dose of 100 mcg/kg IBW/hr has an ideal body weight of 75 kg, has a respiratory rate of 20 breaths per minute (or 1200 breaths per hour):

100 mcg/kg-IBW/hr×75 kg×(1 hr/1200 breaths)×(1,000 ng/mcg)=6250 ng per pulse

In certain embodiments, the 60/respiratory rate (ms) variable may also be referred to as the Dose Event Time. In another embodiment of the invention, a Dose Event Time is 1 second, 2 seconds, 3 seconds, 4 seconds, 5 seconds, 6 seconds, 7 seconds, 8 seconds, 9 seconds, or 10 seconds.

In an embodiment of the invention, a single pulse dose provides a therapeutic effect (e.g., a therapeutically effective amount of NO) to the patient. In another embodiment of the invention, an aggregate of two or more pulse doses provides a therapeutic effect (e.g., a therapeutically effective amount of NO) to the patient.

In an embodiment of the invention, at least about 300, about 310, about 320, about 330, about 340, about 350, about 360, about 370, about 380, about 390, about 400, about 410, about 420, about 430, about 440, about 450, about 460, about 470, about 480, about 490, about 500, about 510, about 520, about 530, about 540, about 550, about 560, about 570, about 580, about 590, about 600, about 625, about 650, about 675, about 700, about 750, about 800, about 850, about 900, about 950, or about 1000 pulses of nitric oxide is administered to a patient every hour.

In an embodiment of the invention, a nitric oxide therapy session occurs over a timeframe. In one embodiment, the timeframe is at least about 1 hour, about 2 hours, about 3 hours, about 4 hours, about 5 hours, about 6 hours, about 7 hours, about 8 hours, about 9 hours, about 10, hours, about 11 hours, about 12 hours, about 13 hours, about 14 hours, about 14 hours, about 15 hours, about 16 hours, about 17 hours, about 18 hours, or about 24 hours per day.

In an embodiment of the invention, a nitric oxide treatment is administered for a timeframe of a minimum course of treatment. In an embodiment of the invention, the minimum course of treatment is about 10 minutes, about 15 minutes, about 20 minutes, about 30 minutes, about 40 minutes, about 50 minutes, about 60 minutes, about 70 minutes, about 80 minutes, or about 90 minutes. In an embodiment of the invention, the minimum course of treatment is about 1 hour, about 2 hours, about 3 hours, about 4 hours, about 5 hours, about 6 hours, about 7 hours, about 8 hours, about 9 hours, about 10, hours, about 11 hours, about 12 hours, about 13 hours, about 14 hours, about 14 hours, about 15 hours, about 16 hours, about 17 hours, about 18 hours, or about 24 hours. In an embodiment of the invention, the minimum course of treatment is about 1, about 2, about 3, about 4, about 5, about 6, or about 7 days, or about 1, about 2, about 3, about 4, about 5, about 6, about 7, or about 8 weeks, or about 1, about 2, about 3, about 4, about 5, about 6, about 7, about 8, about 9, about 10, about 11, about 12, about 18, or about 24 months.

In an embodiment of the invention, a nitric oxide treatment session is administered one or more times per day. In an embodiment of the invention, nitric oxide treatment session may be once, twice, three times, four times, five times, six times, or more than six times per day. In an embodiment of the invention, the treatment session may be administered once a month, once every two weeks, once a week, once every other day, daily, or multiple times in one day.

Timing of a Pulse of NO

In an embodiment of the invention, the breath pattern is correlated with an algorithm to calculate the timing of administration of a dose of nitric oxide.

The precision of detection of an inhalation/inspiration event also permits the timing of a pulse of gas (e.g., NO) to maximize its efficacy by administering gas at a specified time frame of the total inspiration time of a single detected breath.

In an embodiment of the invention, at least fifty percent (50%) of the pulse dose of a gas is delivered over the first third of the total inspiratory time of each breath. In an embodiment of the invention, at least sixty percent (60%) of the pulse dose of a gas is delivered over the first third of the total inspiratory time. In an embodiment of the invention, at least seventy-five percent (75%) of the pulse dose of a gas is delivered over the first third of the total inspiratory time for each breath. In an embodiment of the invention, at least eighty-five (85%) percent of the pulse dose of a gas is delivered over the first third of the total inspiratory time for each breath. In an embodiment of the invention, at least ninety percent (90%) of the pulse dose of a gas is delivered over the first third of the total inspiratory time. In an embodiment of the invention, at least ninety-two percent (92%) of the pulse dose of a gas is delivered over the first third of the total inspiratory time. In an embodiment of the invention, at least ninety-five percent (95%) of the pulse dose of a gas is delivered over the first third of the total inspiratory time. In an embodiment of the invention, at least ninety-nine (99%) of the pulse dose of a gas is delivered over the first third of the total inspiratory time. In an embodiment of the invention, 90% to 100% of the pulse dose of a gas is delivered over the first third of the total inspiratory time.

In an embodiment of the invention, at least seventy percent (70%) of the pulse dose is delivered to the patient over the first half of the total inspiratory time. In yet another embodiment, at least seventy-five percent (75%) of the pulse dose is delivered to the patient over the first half of the total inspiratory time. In an embodiment of the invention, at least eighty percent (80%) of the pulse dose is delivered to the patient over the first half of the total inspiratory time. In an embodiment of the invention, at least 90 percent (90%) of the pulse dose is delivered to the patient over the first half of the total inspiratory time. In an embodiment of the invention, at least ninety-five percent (95%) of the pulse dose is delivered to the patient over the first half of the total inspiratory time. In an embodiment of the invention, 95% to 100% of the pulse dose of a gas is delivered over the first half of the total inspiratory time In an embodiment of the invention, at least ninety percent (90%) of the pulse dose is delivered over the first two-thirds of the total inspiratory time. In an embodiment of the invention, at least ninety-five percent (95%) of the pulse dose is delivered over the first two-thirds of the total inspiratory time. In an embodiment of the invention, 95% to 100% of the pulse dose is delivered over the first two-thirds of the total inspiratory time.

When aggregated, administration of a number of pulse doses over a therapy session/timeframe can also meet the above ranges. For example, when aggregated greater than 95% of all the pulse doses administered during a therapy session were administered over the first two thirds of all of the inspiratory times of all of the detected breaths. In higher precision embodiments, when aggregated greater than 95% of all the pulse doses administered during a therapy session were administered over the first third of all of the inspiratory times of all of the detected breaths.

Given the high degree of precision of the detection methodologies of the present invention, a pulse dose can be administered during any specified time window of an inspiration. For example, a pulse dose can be administered targeting the first third, middle third or last third of a patient's inspiration. Alternatively, the first half or second half of an inspiration can be targeted for pulse dose administration. Further, the targets for administration may vary. In one embodiment, the first third of an inspiration time can be targeted for one or a series of inspirations, where the second third or second half may be targeted for one or a series of subsequent inspirations during the same or different therapy session. Alternatively, after the first quarter of an inspiration time has elapsed the pulse dose begins and continues for the middle half (next two quarters) and can be targeted such that the pulse dose ends at the beginning of the last quarter of inspiration time. In some embodiments, the pulse may be delayed by 50, 100, 150, 200, 250, 300, 350, 400, 450, 500, 550, 600, 650, 700, or 750 milliseconds (ms) or a range from about 50 to about 750 milliseconds, from about 50 to about 75 milliseconds, from about 100 to about 750 milliseconds, or from about 200 to about 500 milliseconds.

The utilization of a pulsed dose during inhalation reduces the exposure of poorly ventilated areas of the lung and alveoli from exposure to a pulsed dose gas, e.g., NO. In one embodiment, less than 5% of poorly ventilated (a) areas of the lung or (b) alveoli are exposed to NO. In one embodiment, less than 10% of poorly ventilated (a) areas of the lung or (b) alveoli are exposed to NO. In one embodiment, less than 15% of poorly ventilated (a) areas of the lung or (b) alveoli are exposed to NO. In one embodiment, less than 20% of poorly ventilated (a) areas of the lung or (b) alveoli are exposed to NO. In one embodiment, less than 25% of poorly ventilated (a) areas of the lung or (b) alveoli are exposed to NO. In one embodiment, less than 30% of poorly ventilated (a) areas of the lung or (b) alveoli are exposed to NO. In one embodiment, less than 50% of poorly ventilated (a) areas of the lung or (b) alveoli are exposed to NO. In one embodiment, less than 60% of poorly ventilated (a) areas of the lung or (b) alveoli are exposed to NO. In one embodiment, less than 70% of poorly ventilated (a) areas of the lung or (b) alveoli are exposed to NO. In one embodiment, less than 80% of poorly ventilated (a) areas of the lung or (b) alveoli are exposed to NO. In one embodiment, less than 90% of poorly ventilated (a) areas of the lung or (b) alveoli are exposed to NO.

Methods of Treatment

In an embodiment of the invention, methods for increasing activity levels in patients with lung-related conditions are described. The methods include administration of iNO, optionally supplementing iNO administration with oxygen. In an embodiment of the invention, iNO is administered according to the pulsed manner discussed herein. In an embodiment of the invention, the iNO is delivered to a patient using the INOpulse® device (Bellerophon Therapeutics). In one embodiment, the patient is administered iNO for a period of at least about 10 minutes, 20 minutes, 30 minutes, 40 minutes 50 minutes, 1 hour, 2 hours, 3 hours, 4 hours, 5 hours, 6 hours, 7 hours, 8 hours, 9 hours, 10 hours, 11 hours, 12 hours, 13 hours, 14, hours, 15 hours, 16 hours, 17 hours, 18 hours, 19 hours, 20 hours, 21 hours, 22 hours, 23 hours, or 24 hours per day for a period of at least about 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks or 20 weeks. In one embodiment, the patient is administered iNO for 8 weeks. In another embodiment, the patient is administered iNO for 16 weeks. In an embodiment of the invention, a nitric oxide therapy session occurs over a timeframe. In one embodiment, the timeframe is at least about 1 hour, about 2 hours, about 3 hours, about 4 hours, about 5 hours, about 6 hours, about 7 hours, about 8 hours, about 9 hours, about 10, hours, about 11 hours, about 12 hours, about 13 hours, about 14 hours, about 14 hours, about 15 hours, about 16 hours, about 17 hours, about 18 hours, or about 24 hours per day.

In an embodiment of the invention, a nitric oxide treatment is administered for a timeframe of a minimum course of treatment. In an embodiment of the invention, the minimum course of treatment is about 10 minutes, about 15 minutes, about 20 minutes, about 30 minutes, about 40 minutes, about 50 minutes, about 60 minutes, about 70 minutes, about 80 minutes, or about 90 minutes. In an embodiment of the invention, the minimum course of treatment is about 1 hour, about 2 hours, about 3 hours, about 4 hours, about 5 hours, about 6 hours, about 7 hours, about 8 hours, about 9 hours, about 10, hours, about 11 hours, about 12 hours, about 13 hours, about 14 hours, about 14 hours, about 15 hours, about 16 hours, about 17 hours, about 18 hours, or about 24 hours. In an embodiment of the invention, the minimum course of treatment is about 1, about 2, about 3, about 4, about 5, about 6, or about 7 days, or about 1, about 2, about 3, about 4, about 5, about 6, about 7, or about 8 weeks, or about 1, about 2, about 3, about 4, about 5, about 6, about 7, about 8, about 9, about 10, about 11, about 12, about 18, or about 24 months.

In an embodiment of the invention, the iNO is administered at anywhere from 10 mcg/kg ideal body weight (IBW)/hr to 200 mcg/kg IBW/hr or more. In one embodiment, the iNO is administered from about 20 mcg/kg IBW/hr to about 150 mcg/kg IBW/hr. In one embodiment, the iNO is administered from about 25 mcg/kg IBW/hr to about 100 mcg/kg IBW/hr. In one embodiment, the iNO is administered from about 30 mcg/kg IBW/hr to about 75 mcg/kg IBW/hr. In one embodiment, the iNO is administered from about 25 mcg/kg IBW/hr to about 50 mcg/kg IBW/hr. In one embodiment, the iNO is administered from about 30 mcg/kg IBW/hr to about 45 mcg/kg IBW/hr. In one embodiment, the iNO is administered at 25 mcg/kg IBW/hr. In one embodiment, the iNO is administered at 30 mcg/kg IBW/hr. In one embodiment, the iNO is administered at 35 mcg/kg IBW/hr. In one embodiment, the iNO is administered at 40 mcg/kg IBW/hr. In one embodiment, the iNO is administered at 45 mcg/kg IBW/hr. In one embodiment, the iNO is administered at 50 mcg/kg IBW/hr. In one embodiment, the iNO is administered at 55 mcg/kg IBW/hr. In one embodiment, the iNO is administered at 60 mcg/kg IBW/hr. In one embodiment, the iNO is administered at 65 mcg/kg IBW/hr. In one embodiment, the iNO is administered at 70 mcg/kg IBW/hr. In one embodiment, the iNO is administered at 75 mcg/kg IBW/hr. In one embodiment, the iNO is administered at 80 mcg/kg IBW/hr. In one embodiment, the iNO is administered at 85 mcg/kg IBW/hr. In one embodiment, the iNO is administered at 90 mcg/kg IBW/hr. In one embodiment, the iNO is administered at 95 mcg/kg IBW/hr. In one embodiment, the iNO is administered at 100 mcg/kg IBW/hr. In one embodiment, the iNO is administered at 105 mcg/kg IBW/kg. In one embodiment, the iNO is administered at 110 mcg/kg IBW/hr. In one embodiment, the iNO is administered at 115 mcg/kg IBW/hr. In one embodiment, the iNO is administered at 120 mcg/kg IBW/hr. In one embodiment, the iNO is administered at 125 mcg/kg IBW/hr. In one embodiment, the iNO is administered at 130 mcg/kg IBW/hr. In one embodiment, the iNO is administered at 135 mcg/kg IBW/hr. In one embodiment, the iNO is administered at 140 mcg/kg IBW/hr. In one embodiment, the iNO is administered at 145 mcg/kg IBW/hr. In one embodiment, the iNO is administered at 150 mcg/kg IBW/hr. In one embodiment, the iNO is administered at 155 mcg/kg IBW/hr. In one embodiment, the iNO is administered at 160 mcg/kg IBW/hr. In one embodiment, the iNO is administered at 165 mcg/kg IBW/hr. In one embodiment, the iNO is administered at 170 mcg/kg IBW/hr. In one embodiment, the iNO is administered at 175 mcg/kg IBW/hr. In one embodiment, the iNO is administered at 180 mcg/kg IBW/hr. In one embodiment, the iNO is administered at 185 mcg/kg IBW/hr. In one embodiment, the iNO is administered at 190 mcg/kg IBW/hr. In one embodiment, the iNO is administered at 195 mcg/kg IBW/hr. In one embodiment, the iNO is administered at 200 mcg/kg IBW/hr.

In an embodiment of the invention, the patient is also administered oxygen with the iNO. In an embodiment of the invention, the oxygen is administered at up to 20 L/minute. In an embodiment of the invention, the oxygen is administered at up to 1 L/minute, 2 L/minute, 3 L/minute, 4 L/minute, 5 L/minute, 6 L/minute, 7 L minute, 8 L/minute, 9 L/minute, 10 L/minute, 11 L/minute, 12 L/minute, 13 L/minute, 14 L/minute, 15 L/minute, 16 L/minute, 17 L/minute, 18 L/minute, 19 L/minute, or 20 L/minute. In an embodiment of the invention, oxygen is administered as prescribed by a physician.

In an embodiment of the invention, the lung related condition useful in the present invention is selected from idiopathic pulmonary fibrosis (IPF), pulmonary fibrosis (PF), interstitial lung disease (ILD), pulmonary arterial hypertension (PAH), chronic obstructive pulmonary disorder (COPD), cystic fibrosis (CF), and emphysema. In an embodiment of the invention, the pulmonary disease is pulmonary hypertension associated with other pulmonary diseases such as Group I-V pulmonary hypertension (PH). In another embodiment, the pulmonary disease and/or lung-related condition is pulmonary hypertension associated with interstitial lung disease. In an embodiment of the invention, the pulmonary disease and/or lung-related condition is pulmonary hypertension associated with pulmonary fibrosis. In an embodiment of the invention, the pulmonary disease and/or lung-related condition is pulmonary hypertension associated with idiopathic pulmonary fibrosis. In an embodiment of the invention, a patient suffering from ILD is at high risk of developing pulmonary hypertension. In another embodiment of the invention, a patient suffering from ILD is at low risk of developing pulmonary hypertension. In an embodiment of the invention, a patient suffering from ILD is at medium risk of developing pulmonary hypertension. In an embodiment of the invention, a patient suffering from IPF is at high risk of developing pulmonary hypertension. In an embodiment of the invention, a patient suffering from IPF is at medium risk of developing pulmonary hypertension. In another embodiment of the invention, a patient suffering from IPF is at low risk of developing pulmonary hypertension. In an embodiment of the invention, a patient suffering from ILD is at high risk of developing pulmonary hypertension. In an embodiment of the invention, a patient suffering from PF is at high risk of developing pulmonary hypertension. In an embodiment of the invention, a patient suffering from PF is at medium risk of developing pulmonary hypertension. In an embodiment of the invention, a patient suffering from PF is at low risk of developing pulmonary hypertension.

Improvements in Pulmonary Arterial Compliance (PAC), Pulmonary Vascular Resistance (PVR), and Pulmonary Arterial Pressure (mPAP)

Pulmonary fibrosis (PF) consists of a wide variety of fibrotic interstitial lung diseases (ILD). Pulmonary hypertension (PH) frequently complicates pulmonary fibrosis (PH-PF) and is associated with significantly worsened clinical outcomes. There are currently no approved therapies to treat PH-PF. PAC describes the pulsatile afterload that accounts for approximately 25% of the total right ventricular (RV) afterload, and a reduction in PAC may initiate and/or exacerbate the distal pulmonary vasculopathy and right ventricular-pulmonary arterial (RV-PA) uncoupling. PAC has been shown to be a strong predictor of outcomes in PAH and every 1-unit (ml/mmHg) reduction resulted in a 17-fold increase in mortality risk. None of the currently available PAH pulmonary vasodilator therapies cause consistent and meaningful improvements in PAC. There is limited data on change in PAC in PH-PF patients. Inhaled NO improves PAC in patients with PH-PF on long term oxygen therapy with intermediate or high probability of PH, as determined by echocardiography.

Methods for reducing pulmonary pressure, reducing pulmonary resistance, and increasing pulmonary arterial compliance are described herein. The method comprises delivering to a patient one or more doses of iNO over a time period. In an embodiment of the invention, the iNO is delivered in one or more pulsed doses. In an embodiment of the invention, the iNO is delivered in one or more dose-escalating pulsed doses. In an embodiment of the invention, the one or more pulsed doses of iNO are delivered over a time period of 180 minutes, 170 minutes, 160 minutes, 150 minutes, 140 minutes, 130 minutes, 120 minutes, 110 minutes, 100 minutes, 90 minutes, 80 minutes, 70 minutes, 60 minutes, 50 minutes, 40 minutes, 30 minutes, 20 minutes, 10 minutes. In an embodiment of the invention, a single dose of iNO is delivered over 10 minutes, 30 minutes, over 60 minutes, or over 90 minutes. In another embodiment, a single dose of iNO is delivered for a period of about 10 minutes. In another embodiment, multiple doses of iNO are delivered over a time period of 10 minutes to about 90 minutes. In an embodiment of the invention, multiple doses of iNO are delivered as described in FIG. 1.

In another embodiment, each dose of iNO is followed by a washout period. In one embodiment, the washout period is from about 1 minute to about 30 minutes. In another embodiment, the washout period is from about 5 minutes to about 25 minutes. In another embodiment, the washout period is from about 10 minutes to about 20 minutes. In another embodiment, the washout period is about 15 minutes. In another embodiment, the washout period is about 10 minutes. In another embodiment, the washout period is about 5, 10, 15, 20, 25, or 30 minutes.

In an embodiment of the invention, the iNO is delivered at a dose of 30 mcg/kg IBW/hr. In another embodiment, the iNO is delivered at a dose of 45 mcg/kg IBW/hr. In another embodiment, the iNO is delivered in a dose of 75 mcg/kg IBW/hr. Example 1 discusses this finding in more detail.

The following pending patent applications are hereby incorporated by references in their entireties: PCT/US2019/032887, filed May 17, 2019; PCT/US2019/045806, filed Aug. 8, 2019; PCT/US2020/013446, filed Jan. 14, 2020; and PCT/US2020/012138, filed Jan. 3, 2020.

While preferred embodiments of the invention are shown and described herein, such embodiments are provided by way of example only and are not intended to otherwise limit the scope of the invention. Various alternatives to the described embodiments of the invention may be employed in practicing the invention.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1: Escalating Doses of Pulsed iNO on PAC as Measured by Right Heart Catheterization (RHC) in Patients with PH Associated with PF (PH-PF)

This study was performed to determine whether increasing doses of pulsed iNO can improve PAC in patients with PH-PF on long-term oxygen therapy with intermediate or high probability of pulmonary hypertension (PH) as determined by echocardiography. Nine patients were acutely challenged with escalating doses of iNO (iNO30, iNO45, and iNO75) over a 90 minute period. Each dose was administered for 10 minutes, with 10 minute "washout" periods between doses. Baseline measurements were taken from timepoint 0-30 minutes. iNO30 was dosed at 30 mcg/kg IBW/hrs from timepoint 30-40 minutes, iNO45 at 45 mcg/kg IBW/hrs from timepoint 50-60 minutes, and iNO75 was dosed at 75 mcg/kg IBW/hrs from timepoint 70-80 minutes (see FIG. 1). The demographics of the patient population is described in Table 1, and Baseline Hemodynamics in Table 2, below.

TABLE 1

| Demographics | |
|---|---|
| Age (yrs) | 66.3 (11.9) |
| Male (%) | 44% |
| FEV1 (% predicted) | 57.8 (14.5) |
| FVC (% predicted) | 56.7 (18.9) |
| DLCO (% predicted) | 25.7 (9.8) |
| Long term $O_2$ therapy (L/min) | 3.8 (1.4) |
| 6 MWD (meters) | 239 (62) |

TABLE 2

| Baseline Hemodynamics | |
|---|---|
| mPAP (mmHg) | 34.7 (8.2) |
| Cardiac Output (L/min) | 3.7 (0.8) |
| PVR (dyne × sec/cm5) | 583 (306) |
| PCWP (mmHg) | 10.0 (3.6) |
| PAC (mL/mmHg) | 1.95 (1.19) |

PAC was derived by stroke volume divided by (SPAP-DPAP) collected during right heart catheterization (RHC). Patients were on sufficient supplemental oxygen at baseline to maintain an SpO2 of at least 92% at rest. Upon completion of the RHC, subjects were offered the opportunity to continue on to chronic iNO therapy in an extension study. 6 minute walk distance (6MWD) was assessed prior to RHC treatment in the extension study.

Figure 3:
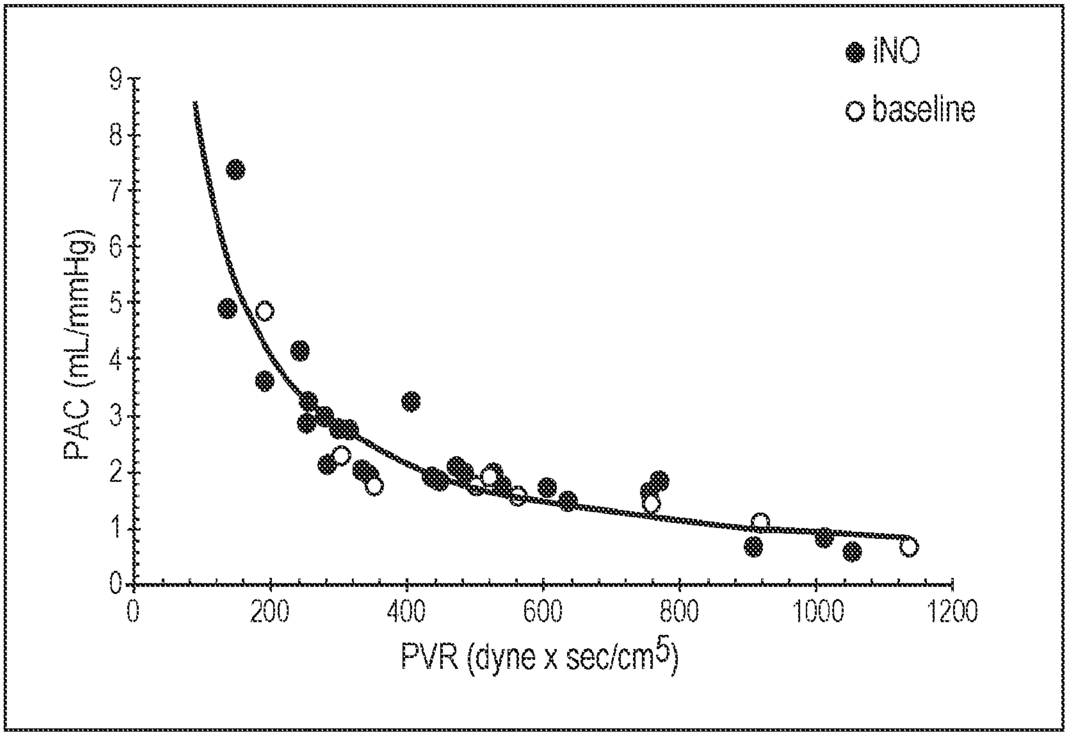
FIG. 3 is a line graph demonstrating resistnace compliance over time. Specifically, PAC and PVR exhibit an expected inverse hyperbolic relationship with a constant resistance compliance time. Subjects on iNO demonstrated an average improvement in PAC above 2 mL/mmHg.

FIGS. 2A-2C demonstrate the results of the study. All subjects demonstrated a reduction in PVR and mPAP with a corresponding increase in PAC on pulsed iNO over their average baseline numbers shown in Table 2. FIG. 2A shows that the change from the average baseline PAC improved with significance for iNO30 and iNO45 doses. FIG. 2B shows that the change from average baseline PVR improved with significance for all three doses, and further improved with significance between the iNO30 and iNO45 doses. FIG. 2C shows that the change from average baseline mPAP improved with significance for all 3 doses. The resistance compliance time curve in FIG. 3 shows that PAC greater than 2 mL/mmHg shifts patients to a more favorable part of the curve. In this example, patients demonstrated an average improvement in PAC of over 2 mL/mmHg. Improvements in PAC were underscored by statistically and clinically significant improvements in PVR and mPAP.

Assessing PAC in patients with normal PVR may allow for early prediction of PH. A reduction in PAC has been shown to predict an increased risk of death even in the presence of normal PVR in some patients. To date, no pulmonary vasodilator has been shown to consistently and significantly improve PAC. The study demonstrates that subjects on iNO demonstrated an average improvement in PAC above 2 mL/mmHG. In group 3 PH patients' therapies that improve PAC without the risk of exacerbating V/Q mismatch may be beneficial in improving RV function.

We claim:

1. A method of reducing pulmonary pressure, the method comprising delivering to a patient two or more doses of inhaled nitric oxide over a time period, wherein the two or more doses of inhaled nitric oxide are dose escalating pulsed doses, wherein a washout period is observed between each dose of the two or more doses, and wherein the washout period is about 1 minute to about 30 minutes.

2. The method of claim 1 wherein the time period is 5, 10, 15, 20, 25, 30, 60, or 90 minutes.

3. The method of claim 1 wherein the dose of inhaled nitric oxide is one or more of a iNO30, iNO45, and iNO75 dose.

4. The method of claim 1 wherein at least fifty percent of the dose of the nitric oxide is delivered over the first third of the total inspiratory time of a breath.

5. The method of claim 1 wherein at least seventy percent of the dose of the nitric oxide is delivered over the first half of the total inspiratory time of a breath.

6. The method of claim 1 wherein at least ninety percent of the dose of the nitric oxide is delivered over the first two-thirds of the total inspiratory time of a breath.

7. A method of reducing pulmonary resistance, the method comprising delivering to a patient two or more doses of inhaled nitric oxide over a time period, wherein the two or more doses of inhaled nitric oxide are dose escalating pulsed doses, wherein a washout period is observed between each dose of the two or more doses, and wherein the washout period is about 1 minute to about 30 minutes.

8. The method of claim 7 wherein the time period is 5, 10, 15, 20, 25, 30, 60, or 90 minutes.

9. The method of claim 7 wherein the dose of inhaled nitric oxide is one or more of a iNO30, iNO45, and iNO75 dose.

10. The method of claim 7 wherein at least fifty percent of the dose of the nitric oxide is delivered over the first third of the total inspiratory time of a breath.

11. The method of claim 7 wherein at least seventy percent of the dose of the nitric oxide is delivered over the first half of the total inspiratory time of a breath.

12. The method of claim 7 wherein at least ninety percent of the dose of the nitric oxide is delivered over the first two-thirds of the total inspiratory time of a breath.

13. A method of increasing arterial compliance, the method comprising delivering to a patient two or more doses of inhaled nitric oxide over a time period, wherein the two or more doses of inhaled nitric oxide are dose escalating pulsed doses, wherein a washout period is observed between each dose of the two or more doses, and wherein the washout period is about 1 minute to about 30 minutes.

14. The method of claim 13 wherein the time period is 5, 10, 15, 20, 25, 30, 60, or 90 minutes.

15. The method of claim 13 wherein the dose of inhaled nitric oxide is one or more of a iNO30, iNO45, and iNO75 dose.

16. The method of claim 13 wherein at least fifty percent of the dose of the nitric oxide is delivered over the first third of the total inspiratory time of a breath.

17. The method of claim 13 wherein at least seventy percent of the dose of the nitric oxide is delivered over the first half of the total inspiratory time of a breath or wherein at least ninety percent of the dose of the nitric oxide is delivered over the first two-thirds of the total inspiratory time of a breath.

* * * * *